(12) United States Patent
Pinza et al.

(10) Patent No.: US 7,667,069 B2
(45) Date of Patent: Feb. 23, 2010

(54) IBOPAMINE MALEATE, METHOD FOR PREPARING IT AND PHARMACEUTICAL COMPOSITIONS CONTAINING IT

(75) Inventors: Mario Pinza, Corsico (IT); Caterina Maugeri, Rome (IT); Nicola Cazzolla, Albano Laziale (IT)

(73) Assignee: Aziende Chimiche Riunite Angelini Francesco A.C.R.A.F.S.p.A., Rome (IT)

( * ) Notice: Subject to any disclaimer, the term of this patent is extended or adjusted under 35 U.S.C. 154(b) by 333 days.

(21) Appl. No.: 10/586,865

(22) PCT Filed: Jan. 13, 2005

(86) PCT No.: PCT/EP2005/000445

§ 371 (c)(1),
(2), (4) Date: Dec. 27, 2006

(87) PCT Pub. No.: WO2005/075409

PCT Pub. Date: Aug. 18, 2005

(65) Prior Publication Data

US 2008/0242724 A1    Oct. 2, 2008

(30) Foreign Application Priority Data

Jan. 30, 2004    (IT) .......................... MI2004A0146

(51) Int. Cl.
*C07C 69/035*    (2006.01)
*A61K 31/32*    (2006.01)

(52) U.S. Cl. ..................................... 560/250; 514/548

(58) Field of Classification Search ....................... None
See application file for complete search history.

(56) References Cited

U.S. PATENT DOCUMENTS 2,400,038 A * 5/1946 Buck et al. .................. 558/269
4,218,470 A   8/1980 Casagrande et al.
4,764,530 A * 8/1988 Carenzi et al. .............. 514/548

FOREIGN PATENT DOCUMENTS

| EP | 0205606  | 12/1986 |
| EP | 0442 958 | 8/1991  |
| WO | 86 03970 | 7/1986  |
| WO | 90 04964 | 5/1990  |

OTHER PUBLICATIONS

Casagrande, C. et al.,"Synthesis and Chemical Properties of Ibopamine and of Related Est of N-Substituted Dopamines-Synthesis of Ibopamine Metabolities", Arzneim.-Forsch./ Drug Res., vol. 36, No. 2a, pp. 291-303, 1986.
Draize, John et al.,"Methods for the Study of Irritation and Toxicity of Substances Applied Topically to the Skin and Mucous Membranes", Pharmacol. Exp. Ther., vol. 83, pp. 377-390, 1944.

* cited by examiner

*Primary Examiner*—Brian J Davis
(74) *Attorney, Agent, or Firm*—Oblon, Spivak, McClelland, Maier & Neustadt, L.L.P.

(57) ABSTRACT

Ibopamine malcate salt (1:1), method for preparing it and pharmaceutical composition containing it.

20 Claims, No Drawings

IBOPAMINE MALEATE, METHOD FOR PREPARING IT AND PHARMACEUTICAL COMPOSITIONS CONTAINING IT

The present invention relates to the salt ibopamine maleate (1:1), to a method for preparing it and to a pharmaceutical composition for ophthalmic use containing it.

U.S. Pat. No. 4,218,470 describes ibopamine (epinine 3,4-O-diisobutyrate) as a drug that is useful in the systemic treatment of- cardiovascular complaints.

EP-A-0 205 606 describes the use of ibopamine and pharmaceutically acceptable acid-addition salts thereof as mydriatics. The pharmaceutically acceptable acid-addition salt specifically illustrated and tested in the said document is the hydrochloride.

EP-A-0 442 958 describes an aqueous pharmaceutical solution for ophthalmic use comprising a pharmaceutically acceptable acid-addition salt of ibopamine, in which the said solution is buffered to pH 4.5 and comprises from 0.1 to 0.5 parts by weight of hydroxypropylmethyl-cellulose per one part by weight of the said ibopamine salt. In this case also, the pharmaceutically acceptable acid-addition salt specifically illustrated and tested is the hydrochloride.

It has now been found that the maleate shows better local tolerability than the hydrochloride.

In a first aspect, the present invention thus relates to ibopamine maleate (1:1).

The salt ibopamine maleate (1:1) is readily prepared via known techniques, for instance the addition of maleic acid, dissolved in a suitable organic solvent, to ibopamine base, also dissolved in a suitable organic solvent, in a 1:1 molar ratio.

The said addition is preferably performed under an atmosphere of an inert gas and at room temperature.

The salt thus formed (ibopamine maleate 1:1) is then isolated via known techniques including the precipitation and filtration of the salt or removal of the solvents by evaporation.

In one preferred embodiment, the abovementioned organic solvent is acetone and the salt is precipitated from the acetone solution via addition of ethyl ether.

In a second aspect, the present invention thus relates to a method for preparing ibopamine maleate (1:1), characterized in that it includes the addition of maleic acid, dissolved in a suitable organic solvent, to ibopamine base, also dissolved in a suitable organic solvent, in a 1:1 molar ratio.

By virtue of its better local tolerability, ibopamine maleate is found to be particularly useful for ophthalmic use for diagnostic and therapeutic purposes.

In a third aspect, the present invention thus relates to a pharmaceutical composition for ophthalmic use, characterized in that it includes ibopamine maleate (1:1) together with at least one pharmaceutically acceptable vehicle.

A typical example of a pathological condition that may find benefit from treatment with a pharmaceutical composition according to the present invention is ocular hypotonia.

For diagnostic purposes, the pharmaceutical composition according to the present invention is advantageously used as a mydriatic.

Preferably, the pharmaceutical composition according to the present invention will be in the form of an ointment or eyedrops and may also comprise other vehicles that are suitable for ophthalmic use, for instance ethylene glycol, PEG, carboxymethylcellulose, mannitol, sorbitol, poloxamers, methylcellulose, hydroxyethylcellulose, hydroxypropylcellulose and the like.

This composition may also comprise other conventional ingredients, for instance: preserving agents, stabilizers, surfactants, buffers, salts for regulating osmotic pressure, emulsifiers, and the like.

If required by particular diagnostic or therapeutic uses, the pharmaceutical composition according to the present invention may comprise other pharmacologically active ingredients whose simultaneous administration is useful, for instance hyaluronic acid.

The amount of ibopamine maleate in the pharmaceutical composition of the present invention may vary within a wide range depending on known factors, for instance the particular diagnostic use or the particular type of disease to be treated, the seriousness of the disease and the number of daily administrations. However, a person skilled in the art may easily and routinely determine the optimum amount.

Typically, the amount of ibopamine in the pharmaceutical composition of the present invention is between 0.01% and 6% by weight and even more preferably between 0.1% and 5% by weight.

The dosage forms of the pharmaceutical composition of the present invention may be prepared according to techniques that are well known to pharmaceutical chemists, including mixing, dissolution, sterilization and the like.

The examples that follow are given to illustrate the present invention without, however, limiting it.

EXAMPLE 1

Preparation of Ibopamine Maleate

Step a)

Saturated sodium carbonate solution was added to a solution of ibopamine hydrochloride (4 g) in water (10 ml) until no further precipitate was formed.

The precipitate was extracted with ethyl ether (50 ml). The organic phase was separated out, dried over sodium sulphate and rapidly filtered through a Büchner funnel. Finally, the ether was removed by evaporation at room temperature and under reduced pressure.

The solid residue thus obtained consisted of ibopamine base (3 g).

Step b)

A solution of maleic acid (674 mg; 0.005 mol) in acetone (5 ml) was added, under an inert atmosphere and without heating, at room temperature, to a solution of ibopamine base (1.78 g; 0.005 mol) in acetone (10 ml).

The solution was left under stirring at room temperature (20 minutes). Ethyl ether was then added dropwise to the formation of opalescence, and stirring was continued until precipitation was complete (30 minutes from the start of the opalescence).

The solid was collected by filtration and washed with ethyl ether. The desired product (1 g) was thus obtained.

m.p.=107-108° C.

| | Elemental Analysis For $C_{21}H_{29}N_1O_8$ | | |
|---|---|---|---|
| | C | H | N |
| Calculated | 59.56 | 6.90 | 3.31 |
| Found | 59.53 | 6.92 | 3.27 |

Test 1

Ocular Tolerability

Two aqueous solutions were used.

The first contained 2% by weight of ibopamine hydrochloride (corresponding to 1.79% by weight of ibopamine) buffered to pH 7.0.

The second contained 2.46% by weight of ibopamine maleate (corresponding to 1.79% by weight of ibopamine) buffered to pH 7.0.

12 male rabbits (New Zealand White) with an average weight of 2 kg and an average age of ten months were used, divided into two groups of six rabbits each. The first group was treated with 0.1 ml of the first test solution three times a day for fifteen days. The second group was treated with 0.1 ml of the second test solution three times a day for fifteen days.

The tolerability was evaluated according to J. Draize et al., Pharmacol. Exp. Ther., 83, 377-390 (1944). The results are shown in Table 1 below.

TABLE 1

| | | Ibopamine hydrochloride | Ibopamine maleate |
|---|---|---|---|
| Conjunctiva | Reddening | 1 | 1 |
| | Swelling | 1 | 0 |
| | Lachrymation | 2 | 1 |
| Iris | | 1 | 0 |
| Cornea | Opacity | 1 | 0 |
| | Area of the cornea affected by opacity | 2 | 1 |
| | Total Score | 8 | 3 |

The invention claimed is:

1. An ibopamine maleate salt having a molar ratio of ibopamine to maleate of 1:1.

2. A pharmaceutical composition comprising:
   the ibopamine maleate salt according to claim 1; and
   at least one pharmaceutically acceptable vehicle.

3. The pharmaceutical composition according to claim 2, wherein the ibopamine maleate salt is present in an amount of 0.01-6 wt. %.

4. The pharmaceutical composition according to claim 2, wherein the ibopamine maleate salt is present in an amount of 0.1-5 wt. %.

5. The pharmaceutical composition according to claim 2, which is in a dosage form selected from the group consisting of an ointment and an eye drop.

6. A mydriatic ophthalmic composition comprising the pharmaceutical composition according to claim 2.

7. A method of inducing mydriasis comprising administering to an eye of a patient the mydriatic ophthalmic composition according to claim 6.

8. A process for preparing the ibopamine maleate salt according to claim 1, wherein said process comprises addition of a maleic acid solution to an ibopamine base solution, wherein the maleic acid solution comprises maleic acid and a first organic solvent, wherein the ibopamine base solution comprises an ibopamine base and a second organic solvent, and wherein the ibopamine base and the maleic acid are in a molar ratio of 1:1.

9. The process according to claim 8, wherein the first organic solvent and the second organic solvent is acetone.

10. The process according to claim 8, wherein said addition is carried out under an inert atmosphere.

11. The process according to claim 8, wherein said addition is carried out at room temperature.

12. The process according to claim 8, wherein said addition is carried out with stirring.

13. The process according to claim 8, wherein said process further comprises isolation of the ibopamine maleate salt.

14. The process according to claim 13, wherein said isolation comprises removal of the first organic solvent and the second organic solvent by evaporation.

15. The process according to claim 13, wherein said isolation comprises precipitation of the ibopamine maleate salt.

16. The process according to claim 15, wherein said precipitation is carried out by addition of a non-solvent.

17. The process according to claim 16, wherein the non-solvent is ethyl ether.

18. The process according to claim 15, wherein said precipitation is carried out by a dropwise addition of a non-solvent with stirring.

19. The process according to claim 18, wherein the non-solvent is ethyl ether.

20. The process according to claim 15, wherein said isolation further comprises filtration of the ibopamine maleate salt.

* * * * *